United States Patent [19]

Bogart

[11] Patent Number: 5,747,770

[45] Date of Patent: May 5, 1998

[54] METHOD OF ENERGY BEAM FORMING SURGICAL INCISION MEMBERS

[75] Inventor: Michael W. Bogart, Milford, Conn.

[73] Assignee: United States Surgical Corporation, Norwalk, Conn.

[21] Appl. No.: 545,191

[22] Filed: Oct. 17, 1995

[51] Int. Cl.[6] .................................................. B23K 26/00
[52] U.S. Cl. ............................ 219/121.72; 219/121.71
[58] Field of Search ........................ 219/121.68, 121.69, 219/121.7, 121.71, 121.18, 121.2, 121.72; 606/222, 223

[56] References Cited

U.S. PATENT DOCUMENTS

| | | |
|---|---|---|
| 4,501,312 | 2/1985 | Matsutani . |
| 4,700,043 | 10/1987 | Matsutani . |
| 4,857,696 | 8/1989 | Taeusch et al. . |
| 4,910,377 | 3/1990 | Matsutani et al. . |
| 4,935,029 | 6/1990 | Matsutani et al. . |
| 4,952,789 | 8/1990 | Suttie . |
| 4,976,727 | 12/1990 | Matsutani et al. . |
| 5,001,323 | 3/1991 | Matsutani et al. . |
| 5,012,066 | 4/1991 | Matsutani et al. . |
| 5,384,945 | 1/1995 | Spingler . |
| 5,569,301 | 10/1996 | Granger et al. ............. 606/223 |

*Primary Examiner*—Geoffrey S. Evans

[57] ABSTRACT

A method for forming a surgical incision member of the type contemplated for use with a suturing apparatus incorporates the use of an energy beam system to form apparatus engaging notched portions in the incision member and a suture receiving aperture. A method is also disclosed for forming an elongated suture receiving bore in a conventional surgical needle utilizing an energy beam system.

15 Claims, 4 Drawing Sheets

METHOD OF ENERGY BEAM FORMING SURGICAL INCISION MEMBERS

BACKGROUND

1. Technical Field

The present disclosure relates to the manufacture of surgical needles and, in particular, to the manufacture of surgical incision members contemplated for use with a surgical suturing apparatus.

2. Description of Related Art

In general, the manufacture of surgical needles involves many processes and machinery to prepare quality needles from raw needle stock. Several of these processes include, inter alia, straightening wire stock, cutting needle blanks from the wire stock, tapering or grinding points on one or both ends of the blank, curving the needle blank to a predetermined radius of curvature and providing structure, e.g., channels, apertures or the like for receiving a suture thread for attachment. As used herein, the term "needle blank" refers to a piece of needle stock at various stages of completion but not fully formed into a surgical grade needle suitable for use during surgical procedures.

The manufacture of surgical incision members, i.e., surgical needles contemplated for use with a surgical suturing apparatus, require specific manufacturing processes in addition to those processes of conventional needles to produce a finished product. Generally, a surgical incision member includes a central body portion and one or more pointed end portions for piercing tissue. The body portion has a centrally located aperture for attachment to a suture and at least one peripherally located groove or notch which is contemplated for engagement with needle engaging blades of a suturing apparatus. Particular surgical incision members are disclosed in U.S. patent application Ser. Nos.: 06/954,013 filed Sep. 30, 1992, entitled SUTURING APPARATUS; and 08/134,145 filed Oct. 8, 1993 entitled SURGICAL SUTURING APPARATUS WITH LOADING MECHANISM, the disclosures of which are incorporated by reference herein. The aforementioned '013 and '145 applications also disclose a suturing apparatus for use with surgical incision members.

One method for manufacturing a surgical incision member of the type disclosed in the aforementioned applications is by a process called metal injection molding or "MIM". The MIM manufacturing process entails the utilization of a mold in forming the incision member. The incision member produced by the MIM process has the apparatus engagement structure (grooves or notches) and the needle attachment aperture formed therein. However, the MIM process tends to be very costly, thus, making it less economically feasible to produce large quantities of the incision members in accordance with this process.

Commonly assigned U.S. patent application Ser. No. 08/320,015, filed Oct. 7, 1994 and entitled PROGRESSIVE DIE APPARATUS FOR FORMING SURGICAL INCISION MEMBERS, the contents of which are incorporated herein by reference, discloses another method and apparatus for manufacturing surgical incision members. The '015 application discloses an apparatus which performs multiple operations including curving of the needle stock, flat and side pressing of the body portion and notching to provide engaging structure for corresponding suturing apparatus. The '015 application also contemplates drilling a suture receiving hole for suture attachment. In accordance with the apparatus disclosed in the '015 application, notching of the blank to form the engaging structure is accomplished with the use of a notching die arrangement. The notching die arrangement is mounted for movement into and out of engagement with a needle blank to impart at least one notch within the blank.

Although the method and die apparatus disclosed in the '015 application is effective in the manufacture of surgical incision members from raw needle stock, the present disclosure is directed to further advancements whereby laser technology is utilized to form the apparatus engaging structure and suture attaching structure.

SUMMARY

Generally stated, the present disclosure is directed to a method for forming a surgical incision member of the type contemplated for use with a suturing apparatus from needle stock. The method includes the steps of providing a needle blank including an elongated body portion having first and second end portions, directing an energy beam at a first peripheral contact surface point of the body portion and maneuvering the energy beam along a path having at least a longitudinal component to a second peripheral contact surface point of the body portion whereby needle material disposed along the path of the energy beam is removed thereby forming a notched portion on the body portion. In a preferred embodiment, two notched portions are formed in the needle blank, one at each end portion. The preferred method also contemplates forming a suture receiving aperture in the needle blank with the energy beam system.

A method is also disclosed for forming an elongated suture receiving bore in a conventional surgical needle.

BRIEF DESCRIPTION OF THE PREFERRED EMBODIMENTS

Preferred embodiments of the disclosure are described herein with reference to the drawings, wherein.

DETAILED DESCRIPTION OF THE PREFERRED EMBODIMENT(S)

Figure 1:
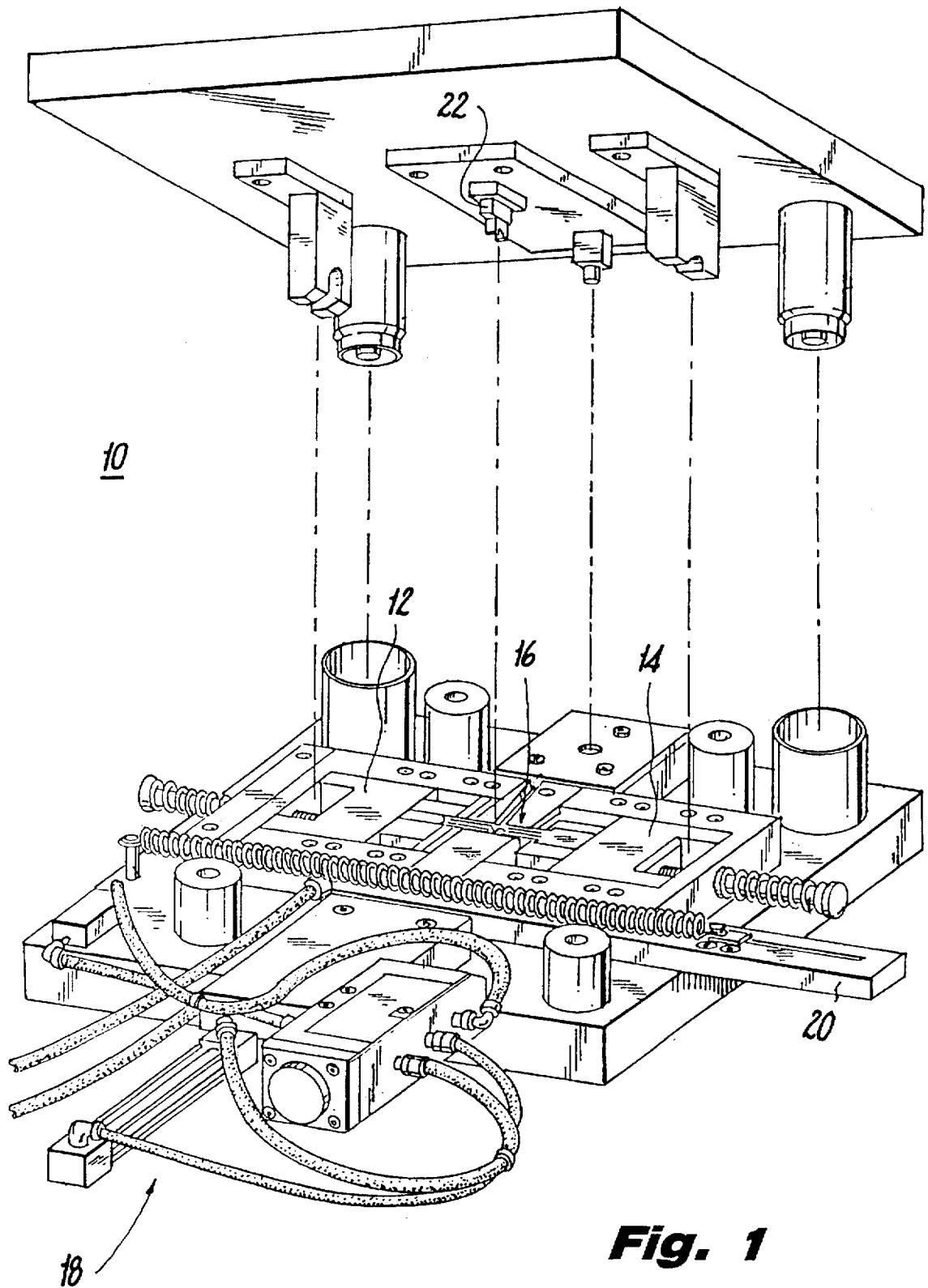
FIG. 1 is a perspective view of an apparatus for forming surgical incision members with the upper and lower portions of the apparatus separated.
Figure 2:
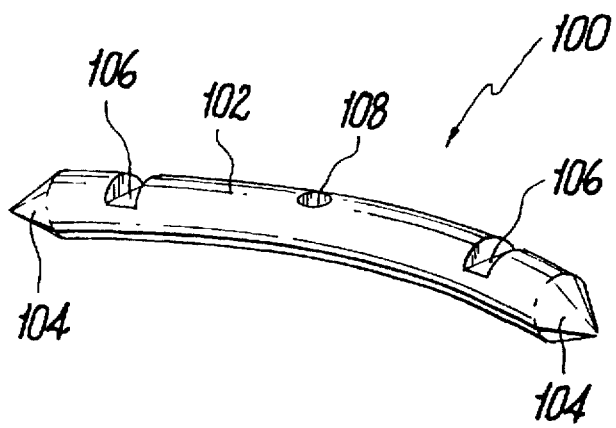
FIG. 2 is a perspective view of a curved surgical incision member produced by the apparatus of FIG. 1 illustrating the instrument engaging notches and the centrally disposed aperture for attachment to a surgical suture.
Figure 3:
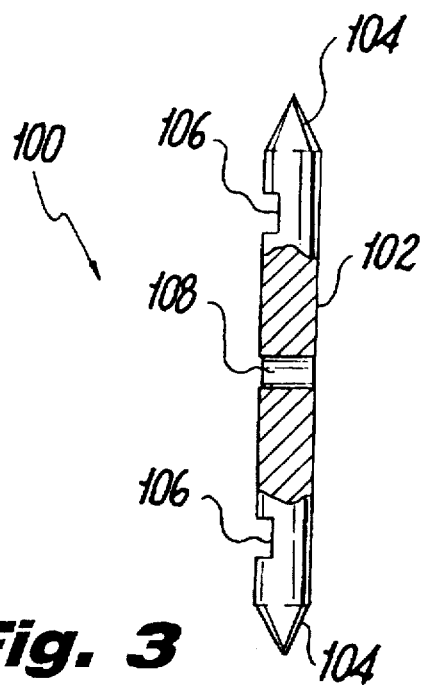
FIG. 3 is a plan view in partial cross-section of the curved surgical incision member of FIG. 2.
Figure 4:
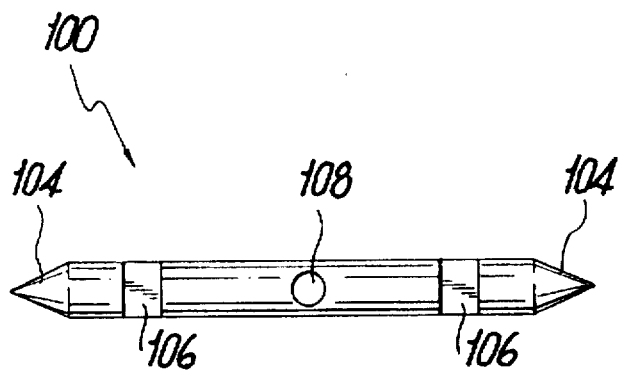
FIG. 4 is a plan view of a straight surgical incision member which may be produced with slight variations to the apparatus of FIG. 1.

Referring now to FIG. 1, there is illustrated an apparatus which is particularly suited to rapidly and precisely form a large number of surgical incision members. This apparatus is disclosed in commonly assigned U.S. patent application Ser. No. 08/320,015, filed Oct. 7, 1994, the contents of which have already been incorporated herein by reference. Apparatus 10 is designed to receive a straight, round bodied and double pointed needle blank and progressively curve the needle blank with appropriate die configurations. Apparatus 10 also imparts apparatus engagement structure, in the form of notched portions, into the needle blank and also contemplates forming a suture receiving aperture in the needle blank. Apparatus 10 may be readily modified to receive precurved needle blanks, or, where straight surgical incision members are desired, dispense with the needle curving structure within the apparatus to produce a straight incision member. FIGS. 2 and 3 illustrate a curved surgical incision member produced by apparatus 10. FIG. 4 depicts a straight incision member which may be produced with slight modifications to the apparatus.

Referring again to FIG. 1, apparatus 10 includes a pair of first and second die mechanisms 12, 14 disposed in a needle forming area 16, which impact the needle blank to provide its curved configuration. A feeding mechanism 18 having a cartridge 20 containing needle blanks is adapted to individually advance needle blanks into needle forming area 16. Apparatus 10 also includes a notching and dimpling die mechanism consisting of notching and upper dimpling die 22 and a lower dimpling die (not shown) which forms the apparatus engaging notched portions and a dimpled area on the needle blank. The dimpled area serves to guide a drill point into engagement with the needle blank thereby facilitating the subsequent drilling of a suture receiving aperture into the blank. The various operations of curving the needle blank, impacting apparatus engagement structure into the blank and dimpling the blank all occur within the centrally located needle forming area 16. Further details of these mechanisms can be ascertained by reference to application Ser. No. 08/320,015.

Alternatively, needle blanks can be formed by the apparatus and method disclosed in U.S. application Ser. No. 08/458,213 filed Jun. 2, 1995 entitled PROGRESSIVE DIE/CARRIER APPARATUS AND METHOD OF FORMING SURGICAL NEEDLES AND/OR INCISION MEMBERS.

Referring now to FIGS. 2 and 3, the surgical incision member formed by the apparatus 10 of FIG. 1 is illustrated. Surgical incision member 100 has a curved body portion 102, as formed by the first and second die mechanisms 12, 14 of apparatus 10, and first and second pointed end portions 104. Adjacent each end portion 104 is a notched portion 106 which engages corresponding structure of a surgical suturing apparatus such as the apparatus disclosed in U.S. patent application Ser. No. 08/134,145, filed Oct. 8, 1993, the contents of which have been already incorporated herein by reference. Also provided is a centrally located aperture 108 which is intended to receive a suture end portion for subsequent attachment. Suture attachment can be accomplished by any conventional methods including the use of adhesives, crimping and the like. FIG. 4 illustrates a straight surgical incision member 100 produced with minor modifications to apparatus 10.

In accordance with a preferred embodiment of the present disclosure, the notching and dimpling die mechanism of apparatus 10 is replaced with a beam energy emitting system to form the apparatus engaging notches 106 on the incision member and the centrally located suture attaching aperture 108. The preferred beam energy emitting system directs an energy beam at the needle blank and maneuvers the energy beam along a predetermined path to form the notches and the attaching aperture. As will be appreciated, apparatus 10 can be modified to incorporate the beam energy emitting system disclosed herein. For example, the beam energy system can be mounted to an upper plate of the apparatus and directed within the central located needle forming area 16. Suitable energy beam emitting systems for this purpose include commercially available laser systems, and a suitable system for controlling movement of the part relative to the beam is a servo-driven numerically controlled multi-axis table.

Figure 5:
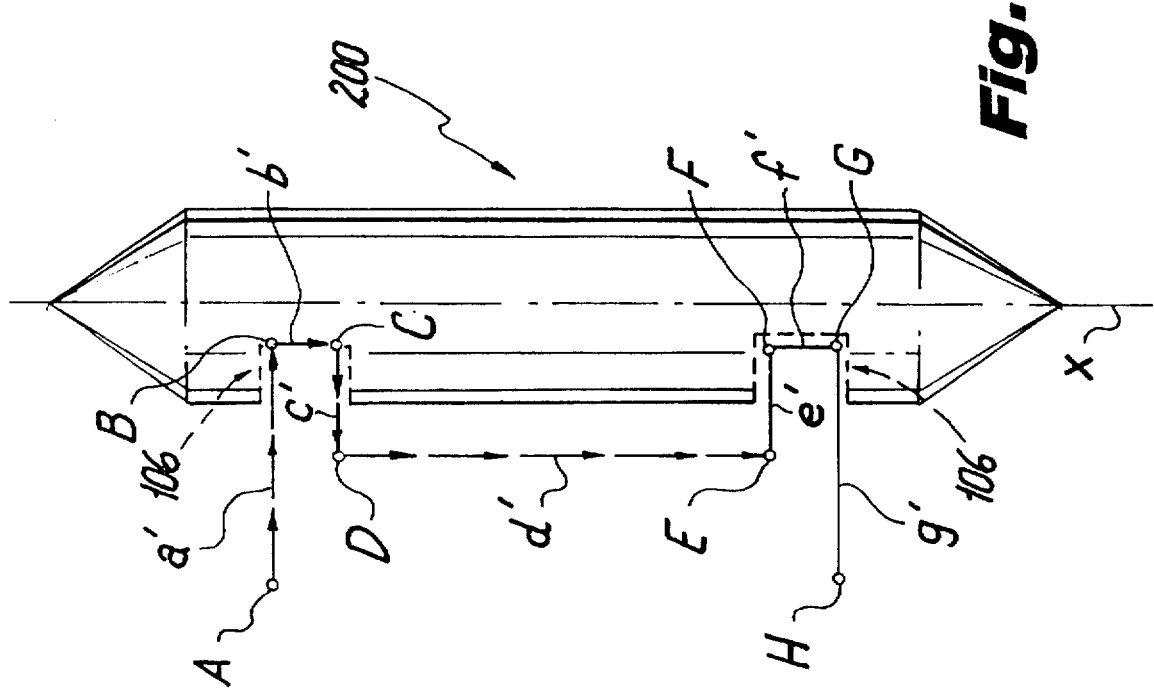
FIG. 5 is a view illustrating the use of an energy beam system to form instrument engaging notches on the incision member.

FIG. 5 diagrammatically illustrates a preferred path of the energy emitting system to produce the two apparatus engaging notches 106 of the curved or straight incision member 100. In FIG. 5, the engaging notches 106 to be formed are illustrated in phantom. In the preferred process, a trepan approach of energy beam cutting is utilized. The trepan approach generally entails maneuvering the energy beam about an enclosed predetermined path to core needle blank material, thus, forming a desired configuration in the needle blank. Thus, a relatively small diameter beam is scanned along a path to cut out the desired material. In the preferred process, the direction of the energy beam relative to the longitudinal axis (i.e., the orientation of the beam relative to the needle) remains constant throughout the path of the beam. With reference to FIG. 5, the energy beam is directed from above the figure and directly into the figure, preferably, transversely thereto.

To commence the energy cutting process, the energy beam is activated at point A and is maneuvered into the body portion of the needle blank 200 along path portion a' as indicated by the arrows. Preferably, path portion a' is generally transverse to the longitudinal axis "x" of the needle blank 200. Upon completing path portion a', the path of the energy beam is changed approximately 90° at point B to follow path portion b' which extends in substantially parallel relation to the longitudinal axis "x" of the needle blank 200. Subsequent to completion of path portion b', the path of the energy beam is again changed approximately 90° at point C to follow path portion c'. The energy beam is maneuvered along path portion c' which extends generally transversely to the longitudinal axis "x" of the needle blank 200 for a predetermined distance to point D where the energy beam is no longer in contact with the needle blank. The energy beam is deactivated and maneuvered along path portion d' to a position adjacent the desired location of the second notched portion, e.g., point E. Thereafter, the energy beam is reactivated and the beam is maneuvered along path portions e', f' and g' in a similar manner to that described in connection with the previously formed notched portion thereby forming the second notched portion in the needle blank. Path portion g' terminates at point H where the energy beam is again deactivated.

It is to be appreciated that any shape or dimensioned notch 106 can be formed in the needle blank 200 by altering the direction of the energy beam and/or increasing or decreasing the predetermined distances traveled in a respective direction. It is also envisioned that the direction of the energy beam may follow a counterclockwise path as well.

Once the two notches 106 are formed in the needle blank 200, the beam energy system also may be utilized to create the suture attachment aperture. The needle blank 200 is rotated 90° along its longitudinal axis "x" such that the newly formed notches 106 directly face the energy beam emitted by the energy beam system. In the alternative, the energy beam system is maneuvered to the appropriate position relative to the needle blank. Of course, the suture attachment aperture could be produced before the notches, if desired.

Figure 6:
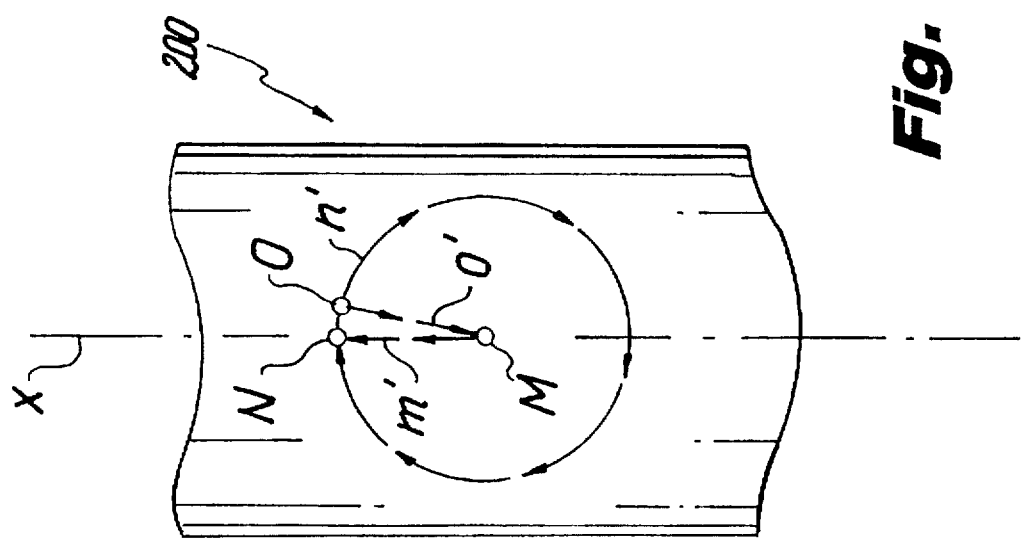
FIG. 6 is a view of the central portion of the incision member illustrating the use of the energy beam system to form the centrally disposed aperture of the incision member.

FIG. 6 diagrammatically illustrates the preferred path of the energy emitting system to form the central suture attachment aperture in the needle blank. FIG. 6 depicts only the central portion of needle blank 200. This preferred process also entails a trepan approach of energy beam cutting. Initially, the energy beam system is directed at point M which preferably corresponds to the midpoint of needle blank 200 and activated. Similar to that described above in connection with the formation of notched portions 106, the preferred direction of the energy beam is generally transverse to the longitudinal axis "x" of the needle blank and remains at the transverse orientation throughout the path of the energy beam. In FIG. 6, the direction of the energy beam is into the figure. Once activated, the energy beam is maneuvered radially outwardly a predetermined distance along path portion m' to point N. The energy beam is then maneuvered along in a clockwise direction along arcuate closed path portion n' which is inclusive of the peripheral contact point N to point O and then maneuvered radially inwardly to return to central point M along path portion o'. Upon completion of the process, a central portion of the needle blank is formed thereby creating the suture receiving aperture 108 in the needle blank 200. In the preferred process, the closed path portion n' is generally circular having a radius equal to the distance of path portion m', thus, defining a generally cylindrically shaped suture receiving aperture in the needle blank 200.

Once the notched portions 106 and suture receiving aperture 108 are formed in the needle blank 200, the needle blank 200 may be transferred to a suture attachment area for attachment to a suture and a new needle blank may be positioned within the needle forming area 16 by feeding mechanism 18 (FIG. 1). In one needle-suture attachment method, a suture is positioned within a suture receiving aperture 108 and the needle portion adjacent the aperture is crimped in accordance with conventional crimping means to form the attachment. In an alternative attachment method, the suture can be adhered within suture receiving aperture 108 with an adhesive. The needle blank may receive subsequent treatments, such as tumbling, polishing, etc., prior to suture attachment.

The energy beam system may be controlled by conventional means to form the desired geometries of notched portions 106 and suture receiving aperture 108. For example, it is contemplated that the energy beam system can be controlled by a computer numerical control (CNC) system whereby the system directs the energy beam along the desired predetermined paths. Other means for controlling the energy beam system are envisioned as well.

Figure 7:
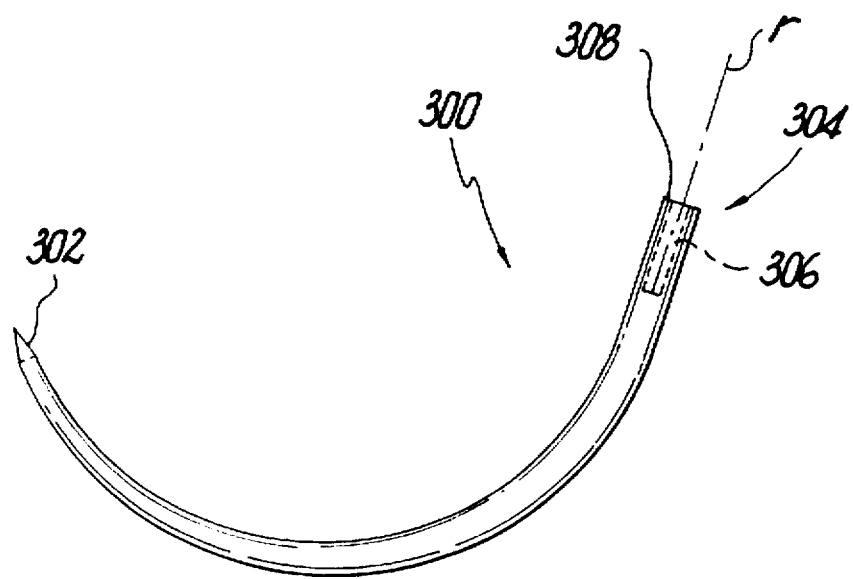
FIG. 7 is a plan view of a curved surgical needle with a pointed end and a blunt end having an elongated suture receiving bore therein where the elongated bore is formed by use of the energy beam system.

It is also envisioned that the trepan approach for energy beam cutting can be utilized to form a needle receiving bore in the blunt end of a conventional surgical needle such as the type shown in FIG. 7. The surgical needle 300 depicted in FIG. 7 includes a pointed end portion 302 and a blunt end portion 304 having an elongated bore 306 formed therein (shown in phantom). The elongated bore 306 receives a surgical suture which is to be attached to the needle 300 by conventional means such as crimping or with the use of adhesives. Typically, the elongated bore 306 is formed by drilling the blunt end face 308 of the needle with a drill or other appropriate instrumentation.

Figure 8:
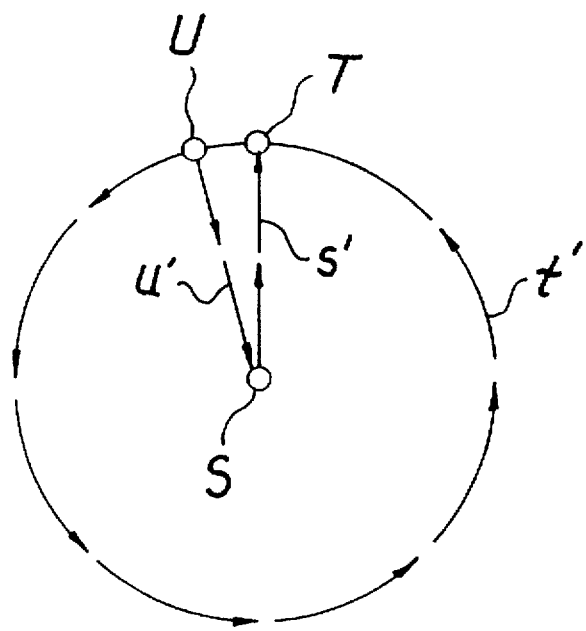
FIG. 8 is an axial view of the blunt needle end of FIG. 7 illustrating the use of the energy beam system to form the elongated bore in the blunt needle end.

In accordance with a preferred method of the present disclosure, the elongated bore 306 may also be formed by utilizing the trepan approach of energy beam cutting. In particular, with reference to FIG. 8, the needle 300 is preferably positioned such that the blunt end face 308 is facing the energy beam emitting system with the direction of the beam in alignment with a longitudinal axis "r" of the blunt end portion 304 as depicted in FIG. 8. The energy beam is activated at central point S and then maneuvered along path portion s' to peripheral contact point T. Thereafter the energy beam is maneuvered along an arcuate closed path portion t' to point U and then maneuvered radially inwardly along path portion u' to return to initial contact point S in a similar manner to that described in forming the suture receiving aperture 108 of the surgical incision members of FIGS. 2-4. Once the elongated bore 306 is formed, the needle can be maneuvered to a suture attachment area for attachment to a suture. Preferably, the energy beam system is moved along a circular path having a radius equal to the distance of s' to form a cylindrical-shaped bore in the needle.

It is contemplated that the present method will provide a product which has undergone less heating and stress in the areas adjacent the notch, aperture or bore formed in the needle blank than if mechanical processes or large diameter laser beams are used to form such structures in the needle blank. Such a result may be advantageous or desirable to the strength and ductility properties of the needle blank, both for further processing such as suture attachment, i.e., crimping, and during use, e.g., interaction with a surgical suturing apparatus and tissue.

Although the subject disclosure has been described with respect to preferred embodiment(s), it will be readily apparent to those having ordinary skill in the art to which it appertains that changes and modifications may be made thereto without departing from the spirit or scope of the subject disclosure as defined by the appended claims.

What is claimed is:

1. A method of forming a surgical incision member from needle stock, comprising the steps of:

a) providing a needle blank including an elongated body portion having first and second end portions, the elongated body portion defining a longitudinal axis;

b) directing an energy beam at a first peripheral contact surface point of the body portion; and c) maneuvering the energy beam along a path having at least a longitudinal component to a second peripheral contact surface point of the body portion whereby needle material disposed along the path of the energy beam is removed thereby forming a notched portion on the body portion.

2. The method according to claim 1 wherein steps (b) and (c) are performed on the first end portion of the needle blank to form a notched portion in the first end portion.

3. The method according to claim 2 wherein steps (b) and (c) are repeated on the second end portion of the needle blank to form a notched portion in the second end portion.

4. The method according to claim 3 further including the step of directing the energy beam at a central portion of the needle blank and maneuvering the energy beam about the central portion along a closed path to remove a portion of the needle blank thereby creating a suture receiving bore therein.

5. The method according to claim 4, wherein the step of directing the energy beam at a central portion includes orienting the energy beam such that the energy beam is generally transverse to the longitudinal axis of the needle blank thereby forming a bore having an axis which is transverse to the longitudinal axis of the needle blank in the central portion of the needle blank.

6. The method of claim 5 wherein the step of maneuvering the energy beam includes maneuvering the energy beam along a circular path to remove a generally cylindrically-shaped portion of the needle blank thereby creating a generally cylindrically-shaped bore therein.

7. The method of according to claim 1 wherein the step of maneuvering includes the steps of:

d) maneuvering the energy beam from the first peripheral contact surface point in a radially inward direction general transverse to the longitudinal axis for a first distance;

e) maneuvering the energy beam in a longitudinal direction in general parallel relation to the longitudinal axis for a second distance; and f) maneuvering the energy beam in a radial outward direction generally transverse to the longitudinal axis for a third distance to the second peripheral contact surface point;

wherein the notched portion formed is generally rectangular shaped.

8. The method according to claim 7 wherein the steps (d)–(f) are performed on the first end portion of the needle blank to form a notched portion in the first end portion.

9. The method according to claim 8 wherein the steps (d)–(f) are repeated on the second end portion of the needle blank to form a notched portion in the second end portion.

10. A method of forming a tissue penetrating member, comprising the steps of:

a) providing a tissue penetrating blank including an elongated portion having first and second end portions, and defining a longitudinal axis;

b) directing an energy beam at a first peripheral contact surface point of the first end portion and maneuvering the energy beam along a path having at least a longitudinal component to a second peripheral contact surface point of the first end portion whereby needle material disposed along the path of the energy beam is removed thereby forming a notched portion in the first end portion;

c) maneuvering the energy beam to the second end portion of the needle blank; and d) directing the energy beam at a first peripheral contact surface point of the second end portion and maneuvering the energy beam along a path having at least a longitudinal component to a second peripheral contact surface point of the second end portion whereby needle material disposed along the path of the energy beam is removed thereby forming a notched portion in the second end portion.

11. A method for forming a bore in a surgical needle blank, comprising the steps of:

providing a needle blank including a body portion having a pointed end portion and a blunt end portion with an end face, the blunt end portion defining a central axis;

applying an energy beam to an initial contact surface point of the end face of the needle blank;

moving the energy beam a predetermined distance from the initial contact surface point to a second surface point of the end face; and maneuvering the energy beam about the end face along a closed path inclusive of the second surface point to remove a portion of the needle blank thereby creating a bore in the blunt end portion.

12. The method of claim 11 further including the step of maneuvering the energy beam to the initial contact surface point.

13. The method of claim 11 wherein the step of maneuvering the energy beam includes maneuvering the energy beam along an arcuate closed path.

14. The method of claim 13 wherein the step of maneuvering the energy beam includes maneuvering the energy beam along a circular path to remove a generally cylindrically-shaped portion of the needle blank thereby creating a generally cylindrically-shaped bore in the blunt end portion.

15. A method of forming a generally cylindrically shaped bore in the blunt end portion of a surgical needle, comprising the steps of:

providing a surgical needle blank including a body portion having a pointed end portion and a blunt end portion with an end face, the blunt end portion defining a central longitudinal axis;

directing an energy beam at an initial contact point of the end face in general alignment with the central longitudinal axis;

moving the energy beam in a radial outward direction from the initial contact point to a second contact point;

maneuvering the energy beam along a circular closed path inclusive of the second contact point; and moving the energy beam in a radial inward direction to the initial contact point to remove a generally cylindrically shaped portion of the needle blank thereby creating a generally cylindrically shaped bore in the blunt end portion.

\* \* \* \* \*